(12) United States Patent
Rossel

(10) Patent No.: US 12,303,582 B2
(45) Date of Patent: May 20, 2025

(54) COMPOSITION FOR THE TREATMENT OF NAIL FUNGUS

(71) Applicant: Oystershell NV, Merelbeke (BE)

(72) Inventor: Bart Rossel, Merelbeke (BE)

(73) Assignee: Oystershell NV, Merelbeke (BE)

( * ) Notice: Subject to any disclaimer, the term of this patent is extended or adjusted under 35 U.S.C. 154(b) by 0 days.

(21) Appl. No.: 17/212,380

(22) Filed: Mar. 25, 2021

(65) Prior Publication Data
US 2021/0299022 A1  Sep. 30, 2021

(30) Foreign Application Priority Data
Mar. 26, 2020 (BE) .................................. 2020/5196

(51) Int. Cl.
| | | |
|---|---|---|
| A61K 8/49 | (2006.01) | |
| A61K 8/33 | (2006.01) | |
| A61K 8/36 | (2006.01) | |
| A61K 8/365 | (2006.01) | |
| A61K 8/37 | (2006.01) | |
| A61K 8/81 | (2006.01) | |
| A61K 9/00 | (2006.01) | |
| A61K 31/19 | (2006.01) | |
| A61K 47/08 | (2006.01) | |
| A61K 47/14 | (2017.01) | |
| A61K 47/22 | (2006.01) | |
| A61K 47/32 | (2006.01) | |
| A61Q 3/02 | (2006.01) | |

(52) U.S. Cl.
CPC .............. *A61K 8/4986* (2013.01); *A61K 8/33* (2013.01); *A61K 8/36* (2013.01); *A61K 8/365* (2013.01); *A61K 8/37* (2013.01); *A61K 8/4973* (2013.01); *A61K 8/8147* (2013.01); *A61K 9/0014* (2013.01); *A61K 31/19* (2013.01); *A61K 47/08* (2013.01); *A61K 47/14* (2013.01); *A61K 47/22* (2013.01); *A61K 47/32* (2013.01); *A61Q 3/02* (2013.01)

(58) Field of Classification Search
CPC .......... A61K 31/19; A61K 47/14; A61K 8/36; A61K 8/37; A61Q 3/02; A61Q 17/005
See application file for complete search history.

(56) References Cited

U.S. PATENT DOCUMENTS

| | | | | | |
|---|---|---|---|---|---|
| 5,830,446 | A | * | 11/1998 | Berthiaume | .......... A61K 8/4966 |
| | | | | | 424/47 |
| 6,143,794 | A | * | 11/2000 | Chaudhuri | ........... A61K 31/137 |
| | | | | | 514/655 |
| 2007/0264293 | A1 | * | 11/2007 | Elder | ..................... A61Q 19/00 |
| | | | | | 424/490 |
| 2008/0112908 | A1 | | 5/2008 | Srulevitch | |

FOREIGN PATENT DOCUMENTS

| | | | | |
|---|---|---|---|---|
| CN | 1357611 A | * | 7/2002 | |
| FR | 2773470 | | 7/1999 | |
| FR | 2939659 A1 | * | 6/2010 | ............... A61K 8/34 |
| FR | 2966359 A1 | * | 4/2012 | ............. A61K 8/375 |
| WO | WO-2007070643 A2 | * | 6/2007 | ............. A61K 31/07 |
| WO | 2011059324 A2 | | 5/2011 | |
| WO | WO-2019045251 A1 | * | 3/2019 | ............... A61K 8/81 |

OTHER PUBLICATIONS

Exi-Nailner (2in1 Nail Polish solution, Jul. 2017, Mintel database) (Year: 2017).*
CN-1357611-A (Espacenet English translation, downloaded Jun. 2022) (Year: 2022).*
FR-2939659-A1 (Espacenet English translation, downloaded Jun. 2022) (Year: 2022).*
FR-2966359-A1 (Espacenet English translation, downloaded 2022) (Year: 2022).*
PubChem (Ethyl lactate, Create date Mar. 26, 2005 and modified date of May 28, 2022, https://pubchem.ncbi.nlm.nih.gov/compound/Ethyl-lactate) (Year: 2022).*
Sleven, Reindert et al (Mycoses: diagnosis, therapy and prophylaxis of fungal diseases, 2016, pp. 1-4 (pp. 1-11 in form provided), (Publishers DOI): http://dx.doi.org/doi:10.1111/MYC.12475), (Year: 2016).*
WO-2019045251-A1 (Google English Translation, downloaded May 2024) (Year: 2024).*
Westerberg et al (American Family Physician, 2013, vol. 88, pp. 762-770C) (Year: 2013).*
Search Report and Written Opinion related to BE2020/5196—English translation of Written Opinion included; dated Nov. 12, 2020.
"Nail Biting Prevention Pen;" www.gnpd.com; Dec. 10, 2015; XP055749679.
"Anti-Fungal Treatment;" www.gnpd.com; Nov. 10, 2015; XP055749683.
"Treatment for Calcic Nails;" www.gnpd.com; Apr. 24, 2015; XP055749684.
"2in1 Nail Polish Solution;" www.gnpd.com; Jul. 21, 2017; XP055749687.

* cited by examiner

*Primary Examiner* — Mark V Stevens
(74) *Attorney, Agent, or Firm* — Vorys, Sater, Seymour and Pease LLP

(57) ABSTRACT

Compositions for the topical treatment of fungal infections in nails, comprising at least one physiologically acceptable carboxylic acid capable of reducing the pH in keratinous tissue, in particular nails, of a treated person below 4.0, preferably in the range of 1.5-4.0, a physiologically acceptable carrier comprising at least one C1-C4 alkyl ester of lactic acid, and at least one physiologically acceptable fluorescent whitening agent. The invention relates to the use of said composition for the preparation of a product suitable for treatment of fungal infections. The invention also relates to the use of said composition for the treatment of a fungal infection.

20 Claims, No Drawings

COMPOSITION FOR THE TREATMENT OF NAIL FUNGUS

FIELD OF THE INVENTION

The invention relates to a composition for topical application. The invention further relates to various uses for the treatment of fungal infections, including and especially focusing on microbiological infections of the nail (onychomycosis). The invention further relates to improving the aesthetic of fungal infections.

BACKGROUND

Onychomycosis is a wide-spread microbiological infection of the nail. The fungi are able to enter the nail through microscopic cracks in the nail. Once in the nail, the fungus starts to degrade the keratin of the nail to feed itself and to alter the environment to its own advantage. One of these alterations includes raising the pH of the nail to an alkaline level. This creates a favorable environment for the fungus in which it can multiply sexually instead of asexually. Also, keratin degradation further enhances spreading of the fungus throughout the nail plate.

US 2008/0112908 discloses anti-fungal nail lacquer comprising glacial acetic acid.

EP 2 498 752 discloses an anti-fungal composition comprising a carboxylic acid and a C1-C4 alkyl ester of lactic acid. Acidification of the nail creates a hostile environment for dermatophytes, thereby blocking the spreading of the infection.

One of the symptoms of fungal infections, is discoloration of the nail (yellowish to green, black). Discoloured nails are considered to have a bad aesthetic. The discoloration often remains until the discolored part of the nail has grown out.

EP 1782 793 discloses a composition for bleaching discolored fingernails. In particular, EP 1 782 793 discloses a composition comprising a hydrogen peroxide generator and a film forming polymer.

Hydrogen peroxide is a strongly oxidizing agent reacts strongly with its environment. This is not desirable in areas infected by a fungus. In particular in combination with nail penetrating agents a high presence of hydrogen peroxide may be experienced as painful by treated persons.

The present invention aims to resolve at least some of the problems and disadvantages mentioned above. The aim of the invention is to provide a method that eliminates those disadvantages. The present invention targets at solving at least one of the aforementioned disadvantages.

The invention thereto aims to provide a composition suitable for treating fungal infections while simultaneously reducing any discoloration.

SUMMARY OF THE INVENTION

The present invention and embodiments thereof serve to provide a solution to one or more of above-mentioned disadvantages. To this end, the present invention relates to a composition according to claim 1.

Such a composition allows the treatment of a fungal infection in keratinous tissue, in particular in nails, while simultaneously reducing discoloration of said nails. This returns nails to a healthy and an aesthetically preferred look as the composition is applied. Treating a nail typically returns the nails natural color, however such a process takes significantly more time.

The use of a fluorescent whitening agent is desired. The inventors have found that such a composition is well tolerated, in contrast to compositions comprising strong oxidizing species such as peroxides. The use of opaque nail lacquers is known to reduce discoloration of nails. However, such nail lacquers may prevent or reduce the ability of treatment compositions to reach within the nail. As a result, a thick nail lacquer can reduce the discoloration but may limit the efficacy of the treatment.

Preferred embodiments of the device are shown in any of the claims 2 to 12

A specific preferred embodiment relates to an invention according to claim 2. In this embodiment, a film-forming polymer is added to the composition. Such a film-forming polymer is a good substrate for the fluorescent whitening agent. It may form a transparent or translucent layer. It is believed and desirable that the fluorescent whitening agent is predominantly comprised within said substrate, in particular a film-forming polymer once the composition is applied to keratinous tissue and the volatile solvents have evaporated.

In a second aspect, the present invention relates to a use according to claim 13. More particular, the use as described herein provides a product suitable for the treatment of fungal infections in keratinous tissue.

Preferred embodiments of the method are shown in any of the claim 14.

In a third aspect, the present invention relates to a use according to claim 15.

An advantage of the present composition is providing privacy for the person to be treated. The application of the composition according to the present invention looks similar to the application of a non-coloured cosmetic nail lacquer. This is desired as people to be treated for fungal infections often prefer privacy with regards to said infection as well as any treatment thereof. The use of the composition according to the present invention can thus be look similar to the application of a cosmetic nail lacquer. It should be noted that the nail lacquer according to the present invention isn't colored and remains transparent. The non-coloured nail lacquer provides the nails with a healthy and natural appearance.

DETAILED DESCRIPTION OF THE INVENTION

The present invention concerns a composition for the topical treatment of fungal infections in nails.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a compartment" refers to one or more than one compartment.

"Comprise", "comprising", and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

The recitation of numerical ranges by endpoints includes all numbers and fractions subsumed within that range, as well as the recited endpoints.

The expression "% by weight", "weight percent", "% wt" or "wt %", here and throughout the description unless otherwise defined, refers to the relative weight of the respective component based on the overall weight of the formulation.

Whereas the terms "one or more" or "at least one", such as one or more or at least one member(s) of a group of members, is clear per se, by means of further exemplification, the term encompasses inter alia a reference to any one of said members, or to any two or more of said members, such as, e.g., any ≥3, ≥4, ≥5, ≥6 or ≥7 etc. of said members, and up to all said members.

Unless otherwise defined, all terms used in disclosing the invention, including technical and scientific terms, have the meaning as commonly understood by one of ordinary skill in the art to which this invention belongs. By means of further guidance, definitions for the terms used in the description are included to better appreciate the teaching of the present invention. The terms or definitions used herein are provided solely to aid in the understanding of the invention.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

The term "nails" as used herein refers not only to human fingernails and/or toenails, but also to similar structures that are present in animals, such as animal nails, hooves, claws, etc.

The terms "fluorescent whitener", "optical brightener", "optical brightening agent", "fluorescent brightening agent" and "fluorescent whitening agent" (FWA) are synonymous herein. Fluorescent whiteners refer to chemical compounds that absorb light in the ultraviolet and violet region (preferably 340-370 nm of the electromagnetic spectrum), and re-emit light in the blue region (preferably 420-470 nm of the electromagnetic spectrum) by fluorescence. This causes a "whitening" effect; they make intrinsically yellow/orange materials look less so, by compensating the deficit in blue and purple light reflected by the material, with the blue and purple optical emission of the fluorophore.

In the first aspect, the invention relates to a composition for the topical treatment of fungal infections in nails, comprising:
at least one physiologically acceptable carboxylic acid capable of reducing the pH in keratinous tissue, in particular nails, of a treated person below 4.0, preferably in the range of 1.5-4.0,
a physiologically acceptable carrier comprising at least one C1-C4 alkyl ester of lactic acid, and
at least one physiologically acceptable fluorescent whitening agent.

In a preferred embodiment of the first aspect, the invention relates to a composition for the topical treatment of fungal infections in nails, comprising:
at least one physiologically acceptable carboxylic acid capable of reducing the pH in keratinous tissue, in particular nails, of a treated person below 4.0, preferably in the range of 1.5-4.0,
a physiologically acceptable carrier comprising at least one C1-C4 alkyl ester of lactic acid,
a physiologically acceptable solvent, and
at least one physiologically acceptable fluorescent whitening agent.

In another preferred embodiment of the first aspect, the invention relates to a composition for the topical treatment of fungal infections in nails, comprising:
at least one physiologically acceptable carboxylic acid capable of reducing the pH in keratinous tissue, in particular nails, of a treated person below 4.0, preferably in the range of 1.5-4.0,
a physiologically acceptable carrier comprising at least one C1-C4 alkyl ester of lactic acid,
a film forming polymer, and
at least one physiologically acceptable fluorescent whitening agent.

In a more preferred embodiment of the first aspect, the invention relates to a composition for the topical treatment of fungal infections in nails, comprising:
at least one physiologically acceptable carboxylic acid capable of reducing the pH in keratinous tissue, in particular nails, of a treated person below 4.0, preferably in the range of 1.5-4.0,
a physiologically acceptable carrier comprising at least one C1-C4 alkyl ester of lactic acid,
a film forming polymer,
a physiologically acceptable solvent, and
at least one physiologically acceptable fluorescent whitening agent.

Carboxylic Acid

The physiologically acceptable acid is a carboxylic acid selected from the group consisting of lactic acid, malic acid, tartaric acid, citric acid, acetic acid, propionic acid, isopropionic acid, oxalic acid, glutaric acid, adipic acid, pyruvic acid, fumaric acid and glycolic acid. Carboxylic acids are capable of achieving the desired pH drop on the infected skin and/or nails, and are typically well tolerated by the treated person.

Most preferably, the carboxylic acid is acetic acid. Acetic acid gives the desired result against onychomycosis and is well tolerated by persons. Another preferred carboxylic acid is lactic acid. Lactic acid gives good results against onychomycosis and is well tolerated. Acetic acid is a relatively cheap compound, in particular compared to lactic acid. An acetic acid/lactic acid combination may also be used.

The carboxylic acid is present in a quantity of at least 1% by weight. In this quantity, the development onychomycosis is effectively hampered. More preferably, the composition comprises at least 1% by weight of acetic acid, more preferably, the composition comprises at least 1.5% by weight of acetic acid, more preferably, the composition comprises at least 2.0% by weight of acetic acid, more preferably, the composition comprises at least 2.5% by weight of acetic acid, most preferably, the composition comprises about 3.0% by weight of acetic acid. In this quantity, the development onychomycosis is severely hindered and, in some cases, even stopped.

Physiologically Acceptable Carrier

The composition includes a solvent consisting of a C1-C4 alkyl ester of a carboxylic acid, which complies with the following structural formula: R1-O—R2, where R1 is a straight or branched alkyl group with one to four and, for example, one to three carbon atoms, and R2 is a group derived from an organic acid or from acetic acid, lactic acid, or formic acid.

More preferably, the composition comprises at least one C1-C4 alkyl ester of lactic acid or acetic acid. The molecular ratio free acid to the ester can be at least 1:100, preferably at least 1:20, most preferably about 1:15. Such C1-C4 alkyl esters are excellent carriers for the carboxylic acid.

The C1-C4 esters include methyl, ethyl, n-propyl, isopropyl, n-butyl, isobutyl, sec-butyl and tert-butyl esters. Ethyl esters are preferred. The C1-C4 alkyl ester is derived from lactic acid or acetic acid.

The C1-C4 alkyl ester is derived from lactic acid or acetic acid. The C1-C4 esters of these acids are particularly effective. The ethyl esters of this compound are preferred. C1-C4 alkyl esters of lactic acid or acetic acid are known to be the most versatile and effective. In a preferred embodiment, the C1-C4 alkyl ester is lactic acid ethyl ester. This compound showed the best results.

In a preferred embodiment, the composition comprises acetic acid as the physiologically acceptable carboxylic acid, and lactic acid ethyl ester as a physiologically acceptable carrier.

In another preferred embodiment, the composition comprises lactic acid as the physiologically acceptable acid, and lactic acid ethyl ester as a physiologically acceptable carrier.

In another preferred embodiment, the composition comprises pyruvic acid as the physiologically acceptable acid, and lactic acid ethyl ester as a physiologically acceptable carrier.

In another preferred embodiment, the composition comprises lactic acid, pyruvic acid and acetic acid as physiologically acceptable acids, using lactic acid ethyl ester as a physiologically acceptable carrier.

In the most preferred embodiment, the composition comprises acetic acid and pyruvic acid as physiologically acceptable acids, using lactic acid ethyl ester as a physiologically acceptable carrier.

These carboxylic acids are physiologically acceptable and well tolerated, permeate well into the keratinous tissue in particular in conjunction with the preferred carrier and any possible penetration enhancing agents. The carboxylic acids are well suited to lower the pH in the human skin and/or nails to the range of 1.5-4.0 and thus the treatment of fungal infections. The invention provides a composition for topical application, including an effective amount of carboxylic acid. The combination of physiologically acceptable carboxylic acid and at least one physiologically acceptable carrier to aid penetration into the nail are known to yield an improved clinical effect in the treatment of fungal infections, in particular the treatment of onychomycosis. It is postulated that fungal infections benefit from the ability of acetic acid in controlling the pH of the nail, an essential part of this formula to combat nail fungus. This is enhanced by presence of the C1-C4 alkyl ester of lactic acid, acetic acid or formic acid as a carrier and stabilizer, which improves the penetration of lactic acid or its derivatives into the skin or nail.

It is preferred that the composition comprises the carboxylic acid and the C1-C4 alkyl ester of a carboxylic acid in an amount of at least 1:50, preferably at least 1:20, more preferably at least 1:15.

In a preferred embodiment, the composition comprises at least 30% by weight of C1-C4 alkyl ester and at least 1% by weight of lactic, acetic acid and/or pyruvic acid. In a more preferred embodiment, the composition comprises at least 35% by weight of C1-C4 alkyl ester and at least 1.5% by weight of lactic, acetic acid and/or pyruvic acid. In a more preferred embodiment, the composition comprises at least 40% by weight of C1-C4 alkyl ester and at least 2.0% by weight of lactic, acetic acid and/or pyruvic acid. In a more preferred embodiment, the composition comprises at least 45% by weight of C1-C4 alkyl ester and at least 2.5% by weight of lactic, acetic acid and/or pyruvic acid.

Fluorescent Whitening Agent

Fluorescent whitening agents for laundry detergents, paper and polymers are well known in the art.

Fluorescent whitening agents include coumarins, in particular those having the following CAS Nos.: [27425-55-4], [12221-86-2], [38215-36-0], [34564-13-1], [62143-26-4], [28754-28-1] and [55470-53-6];

xanthenes, in particular those having the following CAS Nos.: [518-47-8](fluorescein, CI-45350, acid yellow 73), [18472-87-2] (phloxine B, CI-45410), [632-68-8] (rose bengal, CI-45440), [81-88-9] (rhodamine B), [2390-63-8](rhodamine 3B, CI-45175), [52372-39-1] and [52372-36-8];

thioxanthenes, in particular those having the following CAS Nos.: [16294-75-0], [14121-47-2] and [18014-08-9];

azlactones, in particular those having the following CAS Nos.: [25774-09-6] and [51202-86-9];

methines, in particular those having the following CAS Nos.: [23406-34-0] and [84-33-3];

oxazines and thiazines, in particular the product having the following CAS No.: [63589-47-9].

distyrylbenzenes, in particular those having the following CAS Nos.: [13001-39-3], [79026-03-2], [13001-38-2], [36775-00-7], [79026-02-1] and [13001-40-6];

distyrylbiphenyls, in particular those having the following CAS Nos.: [27344-41-8], [51119-63-2], [42380-62-1], [60477-28-3] and [40470-68-6];

divinylstilbenes, in particular those having the following CAS Nos.: [60683-03-6] and [60682-87-3];

coumarins, in particular those having the following CAS Nos.: [91-44-1], [6025-18-9], [19683-09-1], [3333-62-8], [63660-99-1], [26867-94-7] and [52725-14-1];

triazinylaminostilbenes, in particular those having the following CAS Nos.: [3426-43-5], [35632-99-6], [24565-13-7], [12224-16-7], [13863-31-5], [4193-55-9], [16090-02-1], [133-66-4], [68444-86-0], [61968-74-9], [12224-02-1], [99549-42-5], [16470-24-9], [74228-28-7], [83512-97-4] and [76482-78-5];

stilbenzylbenzoxazoles, in particular those having the following CAS Nos.: [18039-18-4] and [64893-28-3];

bis(benzoxazoles), in particular those having the following CAS Nos.: [1041-00-5], [2866-43-5], [7128-64-5], [5089-22-5], [1552-46-1], [1533-45-5] and [5242-49-9];

benzimidazoles, in particular those having the following CAS Nos.: [72829-17-5], [74878-56-1], [74878-48-1] and [66371-25-3];

pyrazolines (1,3-diphenyl-2-pyrazolines), in particular those having the following CAS Nos.: [2744-49-2],

[60650-43-3], [3656-22-2], [27441-70-9], [32020-25-0], [61931-42-8], [106359-93-7], [85154-08-1], [42952-22-7], [63310-12-3], [12270-54-1], [36086-26-7] and [81209-71-4].

Many of the known fluorescent whitening agents are not suitable for use on human skin, hair or nails. In particular not all fluorescent whitening agents are suitable for use in combination with a nail penetrating agent.

In a preferred embodiment, the composition according to the invention includes 2,5-bis(5-tert-butyl-benzoxazol-2-yl) thiophene as fluorescent whitening agent. 2,5-bis(5-tert-butyl-benzoxazol-2-yl)thiophene is known as FWA-184 and has CAS No: [7128-64-5]. It was surprisingly found to be a physiologically acceptable fluorescent whitening agent. It was well tolerated upon nails and provided said nails with a natural and healthy-looking aesthetic.

In a preferred embodiment the fluorescent whitening agent is comprised in the composition in an amount of 0.0001 to 5% by weight, preferably 0.0005 to 1% by weight, more preferably 0.001 to 0.5% by weight, all amounts relative to the weight of the total composition.

Film Forming Polymer

In a preferred embodiment, the composition according to the first aspect of the invention also comprises at least one film-forming polymer. Film-forming polymer may be added to the composition to ensure that the composition, in particular the active ingredients and the fluorescent brightening agent, remain on the nail surface after the solvent has evaporated. This has a dual function. Once dried, the film allows the carboxylic acid and C1-C4 alkyl ester to penetrate through the nail. Furthermore, it provides a suitable substrate for the fluorescent brightening agent to remain on the nail surface. This helps the fluorescent brightening agent to remain on the surface of the nail, rather than penetrating into the nail or washing off.

In the present application, the expression "film-forming polymer" means a polymer which is capable, by itself or in the presence of a film-forming auxiliary, of forming an polymeric film. The at least one film-forming polymer in the composition can be dissolved or dispersed in the form of particles in the composition according to the invention. The at least one film-forming polymer can be insoluble in water at 25° C., i.e., it is soluble at less than 1% by weight in water at 25° C. (solubility of less than 1% by weight). The at least one film-forming polymer can also, for example, be soluble at 25° C. in at least one organic solvent, such as ethyl acetate and methyl acetate, i.e., it is soluble at greater than 90% by weight in at least one organic solvent at 25° C. (solubility greater than 90% by weight at 25° C.).

Representative film-forming polymers that can be used in the composition of the present invention include, but are not limited to, synthetic polymers, radical-mediated types, polycondensate types, and polymers of natural origin.

The expression "radical-mediated film-forming polymer" means a polymer obtained by polymerization of one or more monomers containing unsaturation, in particular ethylenic unsaturation, certain monomers being capable of homopolymerizing (unlike polycondensates).

The at least one film-forming polymer of radical-mediated type can be chosen from vinyl polymers, and vinyl copolymers, in particular acrylic polymers.

The vinyl film-forming polymers can result from the polymerization of monomers containing ethylenic unsaturation having at least one acid group and/or esters of these acidic monomers and/or amides of these acidic monomers.

Representative monomers bearing an acid group which can be used include α, β-ethylenic unsaturated carboxylic acids, such as acrylic acid, methacrylic acid, crotonic acid, maleic acid and itaconic acid, and, in particular, (meth) acrylic acid and crotonic acid. Among these representative monomers, (meth)acrylic acid can be used.

Representative esters of acid monomers include (meth) acrylic acid esters, also known as (meth)acrylates, especially alkyl(meth)acrylates, in particular of a C1-C20 alkyl, such as C1-C8 alkyl; aryl(meth)acrylates, in particular of a C6-C10 aryl; and hydroxyalkyl(meth)acrylates, in particular of a C2-C6 hydroxyalkyl.

Representative alkyl(meth)acrylates include methyl methacrylate, ethyl methacrylate, butyl methacrylate, isobutyl methacrylate, 2-ethylhexyl methacrylate and lauryl methacrylate.

Representative hydroxyalkyl(meth)acrylates include hydroxyethyl acrylate, 2-hydroxypropyl acrylate, hydroxyethyl methacrylate and 2-hydroxypropyl methacrylate.

Representative aryl(meth)acrylates include benzyl acrylate and phenyl acrylate.

Among all these representative examples, the (meth) acrylic acid esters may be the alkyl(meth)acrylates.

According to the present invention, the alkyl group of the esters may be substituted, such as fluorinated or perfluorinated, i.e., some or all of the hydrogen atoms in the alkyl group are substituted with fluorine atoms.

Representative amides of the acid monomers include (meth)acrylamides, and especially N-alkyl(meth)acrylamides, in particular of a C2-C12 alkyl. Representative N-alkyl (meth)acrylamides include N-ethylacrylamide, N-t-butylacrylamide and N-t-octylacrylamide.

The vinyl film-forming polymers can also result from the homopolymerization or copolymerization of at least one monomer chosen from vinyl esters and styrene monomers. In particular, these monomers can be polymerized with acid monomers and/or esters thereof and/or amides thereof, such as those mentioned above.

Representative vinyl esters include vinyl acetate, vinyl neodecanoate, vinyl pivalate, vinyl benzoate and vinyl t-butylbenzoate.

Styrene monomers which may be mentioned are styrene and α-methylstyrene.

The list of monomers given is not limiting and it is possible to use any monomer known to those skilled in the art which falls within the categories of acrylic and vinyl monomers (including monomers modified with a silicone chain).

Polycondensates which can be used as the at least one film-forming polymer can be anionic, cationic, nonionic or amphoteric and are chosen from polyurethanes, polyurethane-acrylics, polyurethane-polyvinylpyrrolidones, polyester-polyurethanes, polyether-polyurethanes, polyureas and polyurea-polyurethanes.

Representative film-forming polyurethanes can be, for example, aliphatic, cycloaliphatic or aromatic polyurethanes, polyurea-urethanes or polyurea copolymers, comprising: (i) at least one sequence originating from monomers chosen from aliphatic monomers, cycloaliphatic monomers, aromatic polyester monomers, branched and non-branched silicone monomers, such as polydimethylsiloxane and polymethylphenylsiloxane, and monomers comprising fluoro groups.

Representative film-forming polycondensates include polyesters, polyesteramides, fatty-chain polyesters, polyamides and epoxyester resins, resins resulting from the condensation of formaldehyde with an arylsulphonamide, and arylsulphonamide epoxy resins.

The polyesters can be obtained, in a known manner, by polycondensation of dicarboxylic acids with polyols, in particular diols.

The dicarboxylic acid can be aliphatic, alicyclic or aromatic. Representative acids include oxalic acid, malonic acid, dimethylmalonic acid, succinic acid, glutaric acid, adipic acid, pimelic acid, 2,2-dimethylglutaric acid, azelaic acid, suberic acid, sebacic acid, fumaric acid, maleic acid, itaconic acid, phthalic acid, dodecanedioic acid, 1,3-cyclohexanedicarboxylic acid, 1,4-cyclohexanedicarboxylic acid, isophthalic acid, terephthalic acid, 2,5-norbornanedicarboxylic acid, diglycolic acid, thiodipropionic acid, 2,5-naphthalenedicarboxylic acid and 2,6-naphthalene-dicarboxylic acid. These dicarboxylic acid monomers can be used alone or in combinations of at least two dicarboxylic acid monomers. Phthalic acid, isophthalic acid, and terephthalic acid can be chosen from among the representative acids.

Representative diols can be chosen from aliphatic, alicyclic, and aromatic diols, such as ethylene glycol, diethylene glycol, triethylene glycol, 1,3-propanediol, cyclohexanedimethanol, and 4-butanediol. Other representative polyols include glycerol, pentaerythritol, sorbitol, and trimethylolpropane.

The polyesteramides can be obtained in a similar manner to the polyesters by polycondensation of diacids with diamines or with amino alcohols. Representative diamines include ethylenediamine, hexamethylenediamine, and meta- and para-phenylene-diamine. A representative amino alcohol is monoethanolamine.

The polyester can also comprise at least one monomer bearing at least one group —$SO_3M$, with M representing a hydrogen atom, an ammonium ion $NH^+$ or a metal ion such as, for example, an $Na^+$, $Li^+$, $K^+$, $Mg^{2+}$, $Ca^{2+}$, $Cu^{2+}$, $Fe^{2+}$, or $Fe^{3+}$ ion. A difunctional aromatic monomer comprising such a group —$SO_3M$ is representative.

The aromatic nucleus of the difunctional aromatic monomer also bearing a group —$SO_3M$ as described above can be chosen, for example, from benzene, naphthalene, anthracene, diphenyl, oxydiphenyl, sulphonyldiphenyl, and methylenediphenyl nuclei. Examples of difunctional aromatic monomers also bearing a group —$SO_3M$ include sulphoisophthalic acid, sulphoterephthalic acid, sulphophthalic acid, and 4-sulphonaphthalene-2,7-dicarboxylic acid.

Copolymers based on isophthalate/sulphoisophthalate, and more particularly copolymers obtained by condensation of diethylene glycol, cyclohexanedimethanol, isophthalic acid, and sulphoisophthalic acid, can be used in the compositions forming the subject of the invention.

Representative optionally modified polymers of natural origin include shellac resins, sandaraque gums, dammar resins, elemis gums, copal resins, and cellulose-derived polymers, such as nitrocellulose, cellulose acetate, cellulose acetobutyrate, cellulose acetopropionate, and ethylcellulose.

In a particular preferred embodiment, the film-forming polymer is a water insoluble substance. More preferably the film-forming polymer selected from the list of polyurethane derivatives, dimethicone, butyl ester of polyvinyl methyl ether and malic acid copolymer, copolymers of acrylates and of ammonium methacrylates, and hydroxy ethyl cellulose, nitrocellulose and ethyl cellulose.

These film-forming polymers are found to be well tolerated, capable of forming translucent or transparent polymer films. These polymer films, at a sufficiently low thickness, are permeable for the carboxylic acid and C1-C4 alkyl ester. This is desired for the continued treatment of the fungal infection by repetitive topical application of the composition. Furthermore, these film-forming polymers are preferred substrates for the fluorescent brightening agent.

In a more preferred embodiment, the film-forming polymer is provided in an amount of 0.05 to 10.0 wt. %, preferably 0.05 to 5.0 wt. % and more preferably 0.05 to 3.0 wt. %, more preferably 0.1 to 3.0 wt. %, more preferably 0.1 to 2.0 wt. %, most preferably 0.1 to 1.0 wt. %, wherein wt. % refers to the weight of the film-forming polymer with respect to the total weight of the composition.

Lower concentrations of film-forming polymer are not sufficient to be a substrate for the carboxylic acid, C1-C4 alkyl ester and fluorescent brightening agent. Lower concentrations of film-forming polymer may also not suffice to form a continuous film on the nail. Higher concentrations lead to a thick polymer film which closes off the nail. This hampers further treatment of said nail. Furthermore, film-forming polymers in this concentration are often translucent or transparent. In a preferred embodiment, the film-forming polymers in is comprised in a concentration such that the resulting film is transparent. The fluorescent brightening agent comprised within the transparent film makes the nails look less yellow/orange/dark and adds more blue to the color. The film-forming polymer thus does not look like an opaque white or coloured cosmetic lacquer but rather provides the nail with a natural, healthy look. This is desired by people to be treated for fungal infection.

Physiologically Acceptable Volatile Solvent

In a preferred embodiment, the composition according to the first aspect further comprises at least one physiologically acceptable volatile solvent. That is to say, the composition according to the first aspect comprises both a C1-C4 alkyl ester of a carboxylic acid and a volatile solvent.

In a particularly preferred embodiment, the composition comprises both a C1-C4 alkyl ester of a carboxylic acid, a film forming polymer and a volatile solvent.

The C1-C4 alkyl ester of a carboxylic acid is a volatile solvent as well as a nail penetrating agent. Addition of another volatile solvent allows better optimization of the evaporation of the composition when applied. This is especially desirable if a thin polymer film is to be obtained.

The volatile solvent as described herein is considered to be an additional solvent, independent from the C1-C4 alkyl ester of a carboxylic acid. The skilled person will understand and appreciate that both the C1-C4 alkyl ester and the volatile solvent act as lipophilic solvent. Both will show evaporation when the composition is topologically applied. However, the evaporation rates may be different.

Examples of suitable physiologically acceptable volatile solvents include, but are not limited to:

a) ketones that are liquid at room temperature, such as methyl ethyl ketone, methyl isobutyl ketone, diisobutyl ketone, isophorone, cyclohexanone, and acetone;

b) alcohols that are liquid at room temperature, such as ethanol, isopropanol, diacetone alcohol, 2-butoxyethanol, and cyclohexanol;

c) glycols that are liquid at room temperature, such as ethylene glycol, propylene glycol, pentylene glycol, and glycerol;

d) propylene glycol ethers that are liquid at room temperature, such as propylene glycol monomethyl ether, propylene glycol monomethyl ether acetate, and dipropylene glycol mono-n-butyl ether;

e) short-chain esters, containing from 3 to 8 carbon atoms in total, such as isopentyl acetate; so long as that said short-chain esters are different from the C1-C4 alkyl ester of a carboxylic acid used as carrier for the physiologically active carboxylic acid.

f) ethers that are liquid at room temperature, such as diethyl ether, dimethyl ether, or dichlorodiethyl ether; this includes acetals that are liquid at room temperature, such as dimethoxy methane (methylal) and dibutoxy methane (butylal).
g) alkanes that are liquid at room temperature, such as decane, heptane, dodecane, and cyclohexane;
h) cyclic aromatic compounds that are liquid at room temperature, such as toluene and xylene;
i) aldehydes that are liquid at room temperature, such as benzaldehyde and acetaldehyde.

In the most preferred embodiment, the physiologically acceptable volatile solvent is dibutoxy methane (butylal). Butylal is well tolerated and evaporates quickly. Furthermore, butylal is a good solvent for the carboxylic acid, C1-C4 alkyl ether as well as any additives, film forming polymers and the fluorescent whitening agent. Additionally, butylal is considered to be an ecological solvent. Lastly, the combination of butylal and ethyl lactate was found to evaporate in a desired and quick manner.

The physiologically acceptable volatile solvent may be present in an amount ranging from 20 to 70% by weight, preferably from 25 to 65% by weight, more preferably from 30 to 60% by weight, more preferably from 35 to 55% by weight, more preferably from 40 to 50% by weight, all weights being based on the total weight of the composition.

In a particularly preferred embodiment, the composition comprises both ethyl lactate and butylal. In a more preferred embodiment, the composition comprises both ethyl lactate and butylal in a ratio of 1:2 to 2:1 by weight, more preferably the composition comprises both ethyl lactate and butylal in a ratio of 1:1.5 to 1.5:1 by weight. Most preferably the composition comprises ethyl lactate and butylal in roughly equal amounts. Quick evaporation and desirable thin polymer films were achieved without impact on the treatment of the nails.

Additives

Preferably, the composition also comprises a nail-penetrating agent. A nail penetrating agent allows the acid and optional other active ingredients to permeate into the nail, which was found to lead to a better inhibition of the growth of nail infections, in particular fungal nail infections.

Preferred nail-penetrating agents are selected from the group consisting of glycols, mono-ethers of glycols, glycolic diethers, dimethylsulfoxide, caprolactam, dimethylisosorbide, isopropylidene glycerol, pentylene glycol, dimethyl-imidazolidinone, N-methylpyrrolidon-2, pyrrolidon-2, ethyl lactate, Cg-ClO polyoxyethylene glycerides, polyethylene glycol glyceryl lactate and dimethylacetamide. The preferred penetrating agent are dimethylisosorbide and ethyl lactate. Mixtures of various nail penetrating agents may be used advantageously.

A preferred embodiment of the composition according to the first aspect of the invention is biotin-containing. Biotin (CAS 58-85-5) is an organic compound with a structure as shown in formula (I):

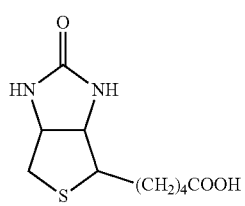

(I)

Biotin is also referred to as vitamin H or vitamin B7.

Biotin is preferably present in the compositions of the present invention in a quantity of 0.001-10% by weight, preferably 0.01-1% by weight, preferably 0.01-0.05% by weight, expressed in relation to the total composition. Being able to dose biotin in lower quantities than is the case with oral composition is economically advantageous as biotin is an expensive ingredient.

To improve the film-forming properties of the composition according to the invention, at least one film-forming auxiliary agent may be provided.

When the at least one film-forming auxiliary agent is used with the at least one film-forming polymer, the at least one film-forming auxiliary agent can be chosen from any compound known to those skilled in the art as being capable of fulfilling the desired function, and can be chosen in particular from plasticizers.

The nail whitening composition disclosed herein may comprise at least one film-forming aid for improving the film-forming properties of the film-forming polymer.

The at least one film-forming aid may be chosen from any compounds known by persons skilled in the art to be capable of fulfilling the desired function, such as those chosen from plasticizing agents.

The plasticizing agents include, but are not limited to:
a) citrates such as triethyl citrate, tributyl citrate, triethyl acetylcitrate, tributyl acetylcitrate, and 2-triethylhexyl acetylcitrate;
b) phthalates such as diethyl phthalate, dibutyl phthalate, dioctyl phthalate, dipentyl phthalate, and dimethoxyethyl phthalate;
c) tricresyl phosphate, benzyl benzoate, tributyl phosphate, butyl acetylricinoleate, glyceryl acetylricinoleate, butyl glycolate, tributoxyethyl phosphate, triphenyl phosphate, dibutyl tartrate, camphor, glyceryl triacetate, N-ethyl-o,p-toluenesulphonamide, and mixtures thereof.

The at least one film-forming aid, such as the plasticizing agent, may be present in an amount, by weight, relative to the total weight of the composition, generally ranging from 0.0001 to 1.5% by weight, preferably from 0.001 to 1.0% by weight, all weights being based on the total weight of the composition.

To improve the skin and nail care and repair function of the composition, the composition may comprise emollients, wetting agents and/or skin conditioners.

In a preferred embodiment, the composition according to the first aspect of the invention comprises a humectant. Preferably the composition comprises a wetting agent selected from the list of: glycerol, C3-C10 glycols such as propylene glycol, butylene glycol, pentylene glycol, hexylene glycol and decylene glycol, sugar alcohols such as glycerol, sorbitol, xylitol and maltitol. These wetting agents acts to moisturize the nails and cuticles. These wetting agents are preferably present in an amount ranging from 0.1 to 8%, preferably from 0.5 to 5% by weight, more preferably from 1.0 to 4.0%, all weights being based on the total weight of the composition.

In another preferred embodiment, the composition according to the first aspect of the invention comprises a perfume. This makes the composition more acceptable to consumers. Furthermore, it reduces the smell of certain carboxylic acids, C1-C4 alkyl ethers, solvents and other volatile organic compounds. This may further allow the treatment composition to be perceived as a cosmetic composition.

In another preferred embodiment, the composition according to the first aspect of the invention comprises an essential oil or botanical extract. Botanical extracts may also be present. Examples of essential oils or botanical extracts include lemon peel extract, essential oil of lemongrass and essential oil of peppermint. Essential oils and botanical extracts may be included as perfume, active ingredient, emollient, etc.

Additional agents may further comprise vitamins, other active or healing agents and treatment agents, colorants and other agents known in the art for either treatment of fungal infection or providing a cosmetic nail lacquer.

Use of the Composition

In a second aspect, the invention relates to the use of a composition according to the invention for the preparation of a product, for instance a medicament, for the treatment of fungal infections. Fungal infections the composition according to the invention may be used against include onychomycosis and other microbiological infections.

The invention relates to the use of a composition according to the invention for the preparation of a product for the treatment of fungal infections.

The invention also relates to the use of a composition according to the invention for the preparation of a product for the treatment of fungal infections in keratinous tissue.

The invention further relates to the use of a composition according to the invention for the preparation of a product for the treatment of onychomycosis.

The invention relates to a device, comprising a container comprising a composition according to the invention, and an applicator connected to the container, wherein the applicator is adapted to apply the composition from the container to a part of human skin and/or nails to be treated.

In a third aspect, the invention relates to the use of a composition according the first aspect of the invention for the treatment of nail infections, in particular superficial, cutaneous and/or subcutaneous mycosis, more preferably the product is for the treatment of onychomycosis or tinea.

EXAMPLES

Example 1

Example 1 is an embodiment of a liquid composition which can be applied to nails of a patient, which composition then solidifies to provide a film-forming layer comprising an optical brightening agent. The composition furthermore comprises a carboxylic acid and a physiologically acceptable carrier suitable for acidifying in the keratinous tissue. A complete list of ingredients and their concentration is provided in Table 1.

This film-forming polymer is an ammonium methacrylate copolymer. This film-forming polymer was found to perform exceptionally well as a film former in nail lacquer applications according to the invention. The film is very strong and adhesive, but also elastic. These properties allow combination of strong nail adhesion and comfort as well as good film-forming properties. In addition, the occlusive film is believed to enhance the hydration of the nail, which in turn stimulates diffusion of acetic acid (polar substance) through the nail. It causes no irritation or redness on the surrounding skin.

FWA-184, also known as OB-184 or 2,5'-Bis[2-(5-tert-buty 1-2 benzoxazoly)thiophene is an optical brightener known for polymers, paints and detergents. It's suitable for use in polymers which come into contact with keratinous tissue and skin. Furthermore, it is stable in the present composition. Furthermore, the combination of film-forming polymer and optical brightener was found to perform exceptionally well to provide a thin non-coloured film and transparent film. It is important that the film-forming polymer is transparent to both visible ranges as well as the wavelengths which are absorbed by the fluorescent whitening agent.

Acetic acid, $CH_3COOH$, also known as ethanoic acid, acts as acidifying agent. Its small size and its hydrophilic properties enables it to penetrate the nail quickly and lower the pH efficiently. Furthermore, its low molecular weight means there are more acid molecules per weight unit, meaning it will take more alkaline substance to neutralize it than larger acids (such as propionic acid or lactic acid). This enables the acid to keep the pH low for a longer period of time, when taking into account the same compensatory production or liberation of alkaline products. This small acid penetrates the nail and lowers the pH of the nail plate, thus preventing fungal development. Although dermatophytes are not necessarily alkaliphilic, they cannot grow under continuous acidic conditions.

The composition showed to be a good-flowing, smooth, homogeneous phase.

TABLE 1 composition according to example 1

| ingredient | content (wt.%) |
| --- | --- |
| acetic acid | 3 |
| pyruvic acid | 0.05 |
| ethyl lactate | 45 |
| ammonium methacrylate copolymer | 0.1 |
| optical brightener FWA-184 | 0.01 |
| butylal | 51.84 |

Example 2

Example 2 is a composition similar to example 1, which was further improved by the addition of dimethyl isosorbide, a penetration enhancer allowing complete penetration of the acid into the nail. The composition is shown in table 2.

TABLE 2 composition according to example 2

| ingredient | content (wt.%) |
| --- | --- |
| acetic acid | 3 |
| pyruvic acid | 0.05 |
| ethyl lactate | 45 |
| ammonium methacrylate copolymer | 0.1 |
| optical brightener FWA-184 | 0.01 |
| Dimethyl isosorbide | 3.0 |
| butylal | 48.84 |

Example 3

Example 3 is a composition similar to previous examples, which was modified by a higher concentration of film-forming polymer. The composition is shown in table 3. It was noted that the composition was no longer a homogeneous phase. The film-forming polymer does not dissolve into the composition entirely.

TABLE 3 composition according to example 3

| ingredient | content (wt.%) |
|---|---|
| acetic acid | 3 |
| pyruvic acid | 0.05 |
| ethyl lactate | 45 |
| ammonium methacrylate copolymer | 0.5 |
| optical brightener FWA-184 | 0.01 |
| butylal | 51.44 |

Example 4

Example 4 is a composition similar to previous examples, which was modified by a higher concentration of film-forming polymer in ethyl lactate. The composition is shown in table 4. It was noted that in the present composition, the film-forming polymer does dissolve entirely.

The skilled person understands that different combinations of polymer and composition, will have a different phase. A good-flowing, smooth and homogeneous liquid phase is preferred for the application of the composition to a nail, allowing the formation of a smooth film and optimal product performance, respectively.

TABLE 4 composition according to example 4

| ingredient | content (wt.%) |
|---|---|
| acetic acid | 3 |
| pyruvic acid | 0.05 |
| ethyl lactate | 96.44 |
| ammonium methacrylate copolymer | 0.5 |
| optical brightener FWA-184 | 0.01 |

Example 5

Example 5 is a composition similar to previous examples, which was further improved by addition of various additives and further ingredients. The composition is shown in table 5. The composition showed to be a good-flowing, smooth, homogeneous phase.

The skilled person understands that different combinations of polymer and composition, will have a different phase. A good-flowing, smooth and homogeneous liquid phase is preferred for the application of the composition to a nail, allowing the formation of a smooth film and optimal product performance, respectively.

Peppermint oil is added as fragrance and solvent for different ingredients. Second to this, penetration capacity is enhanced by inclusion of peppermint oil. Furthermore, it mitigates the odour of the included organic acids.

Decylene glycol has different functions: conditioning, emollient, humectant, solvent and preservative booster.

Polysorbate 80, cetyl acetate, acetylated lanolin alcohols is a solubilized acetylated lanolin alcohol derivative in a concentration of 0.5 to 5.0%. It is a mixture of polysorbate 80, cetyl acetate, stearyl acetate, oleyl acetate and acetylated lanolin alcohol. It is a superfatting agent to help to prevent dryness of the skin surrounding the nail.

Biotin, also known as vitamin $B_7$, vitamin H or coenzyme R is necessary for cell growth, the production of fatty acids, isoleucine and valine. It also plays a role in gluconeogenesis. Biotin assists in various metabolic reactions involving the transfer of carbon dioxide. As the nails that are suffering from onychomycosis are very brittle and dull, biotin helps to reestablish the growth of a healthy nail by supporting the cell metabolism. This allows the nail to cure faster and to be less prone to reinfection.

Cholesterol, ceramides and fatty acids are beneficial for skin conditioning and repair. They aid in improving the appearance of skin smoothness, laxity and pores. It helps provide healthy and aesthetically pleasing skin surrounding the nail.

TABLE 5 composition according to example 5

| ingredient | content (wt.%) |
|---|---|
| Ethyl lactate | 45 |
| Ammonium Methacrylate Copolymer | 0.1 |
| Decylene glycol | 3 |
| Butylal | 41.67 |
| Acetic acid | 3 |
| Pyruvic acid | 0.1 |
| dimethyl isosorbide | 1 |
| Polysorbate 80, cetyl acetate and acetylated lanolin alcohols | 3 |
| Peppermint oil | 3 |
| Cholesterol | 0.1 |
| FWA-184 | 0.01 |
| Biotin | 0.02 |

The invention claimed is:

1. A method for treatment of a fungal infection, the method comprising: applying a composition to a nail of a person to be treated wherein said nail has a fungal infection and a resulting discoloration, said composition including:
   at least one physiologically acceptable carboxylic acid capable of reducing the pH in the nail of the treated person below 4.0,
   a physiologically acceptable carrier comprising at least one C1-C4 alkyl ester of lactic acid and optionally at least one additional volatile solvent,
   a film-forming polymer provided in a quantity of 0.05 to 10% by weight of the composition; wherein the film-forming polymer comprises ammonium methacrylate copolymer; and at least one physiologically acceptable fluorescent whitening agent comprising 2,5-bis (5-tert-butyl-benzoxazol-2-yl) thiophene (FWA-184),
   wherein, upon evaporation of the physiologically acceptable carrier, the applied composition forms a solidified film layer in contact with the nail;
   wherein the applied composition treats the fungal infection and reduces the appearance of the resulting discoloration, and
   wherein the applied composition has a whitening effect.

2. The method according to claim 1, wherein the fungal infection is cutaneous mycosis, subcutaneous mycosis, or a combination thereof.

3. The method according to claim 1, wherein the fungal infection is onychomycosis or tinea.

4. The method according to claim 1, wherein said at least one physiologically acceptable fluorescent whitening agent is present in a quantity of at least 0.005% by weight of the composition.

5. The method according to claim 1, wherein said film-forming polymer is an ammonium methacrylate copolymer.

6. The method according to claim 1, wherein said film-forming polymer is present in a quantity from 0.1 to 10.0% by weight of the composition.

7. The method according to claim 1, wherein said composition further includes butylal as a physiologically acceptable solvent.

8. The method according to claim 1, wherein said at least one physiologically acceptable carboxylic acid is selected from the group consisting of lactic acid, malic acid, tartaric acid, citric acid, acetic acid, propionic acid, isopropionic acid, oxalic acid, glutaric acid, adipic acid, pyruvic acid and glycolic acid.

9. The method according to claim 1, wherein said at least one carboxylic acid is pyruvic acid.

10. The method according to claim 1, wherein said at least one C1-C4 alkyl ester of lactic acid is ethyl lactate.

11. The method according to claim 1, wherein the composition further comprises a nail penetrating agent that is dimethyl isosorbide.

12. The method according to claim 1, wherein the composition further comprises an additive selected from the group consisting of an emollient, wetting agent, a skin conditioner, and a combination thereof.

13. The method according to claim 1, wherein the composition comprises at least 30% by weight of the composition of the at least one C1-C4 alkyl ester of lactic acid and at least 1% by weight of the composition of the at least one physiologically acceptable carboxylic acid.

14. The method according to claim 1, wherein the at least one physiologically acceptable carboxylic acid is lactic acid, acetic acid, pyruvic acid, or a combination thereof.

15. The method according to claim 1, wherein a molecular weight ratio of the at least one physiologically acceptable carboxylic acid to the at least one C1-C4 alkyl ester of lactic acid is at least 1:20.

16. The method according to claim 1, wherein said at least one C1-C4 alkyl ester of lactic acid is ethyl lactate, and wherein said composition further includes butylal as a physiologically acceptable solvent.

17. The method according to claim 16, wherein the ethyl lactate and the butylal are in a ratio by weight of 1:2 to 2:1.

18. The method according to claim 1, wherein said applied composition whitening effect reduces the appearance of the resulting discoloration by reducing any yellow or orange or dark appearance of the nail and/or by adding blue to the color of the nail.

19. The method according to claim 1, wherein reducing the appearance of the resulting discoloration gives the nail a healthy and a natural appearance.

20. The method of claim 1, wherein the solidified layer is transparent and/or noncoloured.

* * * * *